United States Patent
Jordan

(10) Patent No.: US 9,415,196 B2
(45) Date of Patent: Aug. 16, 2016

(54) PANCREATIC STENT DRAINAGE SYSTEM

(71) Applicant: Boston Scientific Scimed, Inc., Maple Grove, MN (US)

(72) Inventor: Gary Jordan, Litchfield, NH (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 14/200,878

(22) Filed: Mar. 7, 2014

(65) Prior Publication Data

US 2014/0277561 A1 Sep. 18, 2014

Related U.S. Application Data

(60) Provisional application No. 61/779,848, filed on Mar. 13, 2013.

(51) Int. Cl.
*A61M 27/00* (2006.01)
*A61F 2/04* (2013.01)
*A61F 2/82* (2013.01)

(52) U.S. Cl.
CPC ............... *A61M 27/002* (2013.01); *A61F 2/04* (2013.01); *A61F 2/82* (2013.01); *A61M 27/008* (2013.01); *A61M 2210/1057* (2013.01)

(58) Field of Classification Search
CPC ............. A61M 27/002; A61M 27/008; A61F 2002/061
USPC .......................... 623/23.64, 23.69, 23.7, 1.27
See application file for complete search history.

(56) References Cited

U.S. PATENT DOCUMENTS

| | | | |
|---|---|---|---|
| 6,001,123 A * | 12/1999 | Lau | 623/1.12 |
| 6,355,063 B1 * | 3/2002 | Calcote | 623/1.42 |
| 7,214,229 B2 | 5/2007 | Mitchell et al. | |
| 7,217,250 B2 | 5/2007 | Kolb | |
| 7,338,530 B2 | 3/2008 | Carter et al. | |
| 7,470,247 B2 | 12/2008 | Aliski et al. | |
| 7,507,218 B2 | 3/2009 | Aliski et al. | |
| 7,637,942 B2 | 12/2009 | Mangiardi et al. | |
| 7,757,691 B2 | 7/2010 | Reynolds et al. | |
| 7,875,068 B2 | 1/2011 | Mangiardi et al. | |
| 7,887,579 B2 | 2/2011 | Mangiardi et al. | |
| 8,221,186 B2 | 7/2012 | Policaro et al. | |
| 8,221,505 B2 | 7/2012 | Skerven | |
| 8,262,721 B2 | 9/2012 | Welborn et al. | |
| 8,323,350 B2 | 12/2012 | Nissl | |
| 8,366,650 B2 | 2/2013 | Young | |
| 8,475,516 B2 | 7/2013 | Paul et al. | |
| 8,481,138 B2 | 7/2013 | Miller et al. | |
| 8,511,310 B2 | 8/2013 | Reynolds et al. | |
| 8,535,259 B2 | 9/2013 | Thompson | |
| 8,585,753 B2 | 11/2013 | Scanlon et al. | |
| 8,603,185 B2 | 12/2013 | Shah et al. | |
| 8,753,407 B2 | 6/2014 | Nguyen | |
| 2006/0247761 A1 * | 11/2006 | Greenberg et al. | 623/1.16 |
| 2010/0100170 A1 | 4/2010 | Tan et al. | |

* cited by examiner

*Primary Examiner* — Thomas J Sweet
*Assistant Examiner* — Daniel Bissing

(57) ABSTRACT

The present invention relates to a medical device, for pancreas, equipped with drainage feature. The medical device includes a stent having an exterior surface, a proximal end and a distal end. The medical device further includes a drainage tube helically wrapped around the stent. The drainage tube includes an external surface, an internal surface, a proximal end, and a distal end. The external surface of the drainage tube is designed with a plurality of holes. The pluralities of holes are connected to the internal surface via a lumen. The plurality of holes can be configured to direct the fluid from side walls of pancreas and bring it out through lumen to avoid occlusion of the side walls in pancreas.

16 Claims, 7 Drawing Sheets

PANCREATIC STENT DRAINAGE SYSTEM

CROSS-REFERENCE TO RELATED APPLICATIONS

This application claims the benefit of and priority to U.S. Provisional Application No. 61/779,848, filed Mar. 13, 2013, the entire contents of which are herein incorporated by reference.

FIELD

The present invention relates to bodily fluid drainage, more particularly, to a pancreatic stent drainage system.

BACKGROUND

Pancreatic endotherapy has been used for years for treatment of several types of pancreatic disorders including but not limited to chronic pancreatitis, idiopathic acute recurrent pancreatitis, and many such others.

Normally, inside the human body the pancreas is connected to the duodenum via the pancreatic duct. The pancreatic duct abuts the sphincter of Oddi, which connects the pancreatic duct to the duodenum. The pancreatic duct delivers to the duodenum pancreatic fluids required for metabolism. In various pancreatic disorders, pancreatic tissues may swell or increase abnormally thereby constricting the pancreatic duct and obstructing flow of pancreatic fluids into the duodenum. Such obstructions could lead to various complications including those arising from the accumulation of pancreatic fluids inside the pancreatic tissue or the pancreatic duct. In such cases, an intraluminary prosthesis, such as a stent, may be used for treatment of the obstructed pancreatic duct. The stent provides an outwardly-directed radial force that opens the constriction of the pancreatic duct thereby allowing pancreatic fluid to flow into the duodenum. In some cases, at least a portion of the stent is placed proximal to the sphincter of Oddi and adjacent to ampulla of Vater near and inside head region of the pancreas in a patient's body.

Intraluminal stents within the pancreatic duct are associated with several drawbacks including stent migration and blockage of side branches of the pancreatic duct. Blockage of pancreatic duct side branches can impede flow of pancreatic fluids and result in chronic pancreatitis. Some pancreatic stents are polymer tubes that have side holes helically placed along a length of the stent. The side holes allow pancreatic fluid to flow into the lumen of the stent thereby reducing the incidence of side branch occlusion while still allowing for stent removal at a future time. An example of a intraluminal pancreatic stent is provided in U.S. Pat. No. 6,132,471, which is incorporated herein by reference.

Recently physicians are looking to metal stents for use in the pancreas. Expandable metal stents provide substantially consistent outward radial force over time, which allows the stent to expand as duct constriction is relieved. In this way, metal stents avoid the need to exchange the stents multiple times, each time for a progressively larger diameter stent, until the desired dilation of the pancreatic duct is achieved. Another benefit of metal stents is a greater patency rate.

A concern with metal stents is that surrounding tissue may grow into the stent, complicating stent removal and compromising the stent lumen. For this reason metal stents are often coated with a polymeric covering that reduces growth of host tissue into the interstices of the metal stent. Coated metal stents allow for easier and less traumatic stent removal. Unfortunately, coated stents are more susceptible to stent migration, which can result in the stent exiting the treatment site.

Coated stents are also more likely to occlude pancreatic fluid flow within side branches of the pancreatic duct. Pancreatic fluid flows to the duodenum through a network of branching upstream ducts that converge into a central pancreatic duct. Coated stents placed in a downstream pancreatic duct may block the mouth of an upstream tributary duct that empties into the downstream duct. In this way, a coated stent could dam an upstream network of ducts. Impeding the flow of pancreatic fluid can harm the pancreas and result in pancreatitis.

Thus, there exists a need for a stent with an additional drainage system to avoid occlusion of upstream ducts while reducing the likelihood of stent migration.

Without limiting the scope of the invention, a brief summary of some of the claimed embodiments of the invention is provided below. Additional details of the summarized embodiments of the invention and/or additional embodiments of the invention can be found in the detailed description of the invention.

A brief abstract of the technical disclosure in the specification is provided as well for the purposes of complying with 37 C.F.R. 1.72. The abstract is not intended to be used for interpreting the scope of the claims.

All US patents and applications and all other published documents mentioned anywhere in this application are incorporated herein by reference in their entirety.

SUMMARY

In at least one embodiment, the present invention relates to a medical device equipped with a drainage feature. The medical device includes a stent having an outer surface, a proximal end, and a distal end. The medical device further includes a drainage tube. The drainage tube includes an internal surface, an external surface, a distal end, and a proximal end. In an embodiment, the drainage tube is configured to be attached to the outer surface of the stent. The medical device is configured such that the proximal end of the drainage tube is positioned adjacent to the proximal end of the stent. Further, the external surface of the drainage tube is configured to include a plurality of holes. The holes on the outer surface of the drainage tube are connected to the internal surface of the drainage tube.

BRIEF DESCRIPTION OF THE FIGURES

The invention and the following detailed description of certain embodiments thereof can be understood with reference to the following figures.

DETAILED DESCRIPTION

Figure 1A:
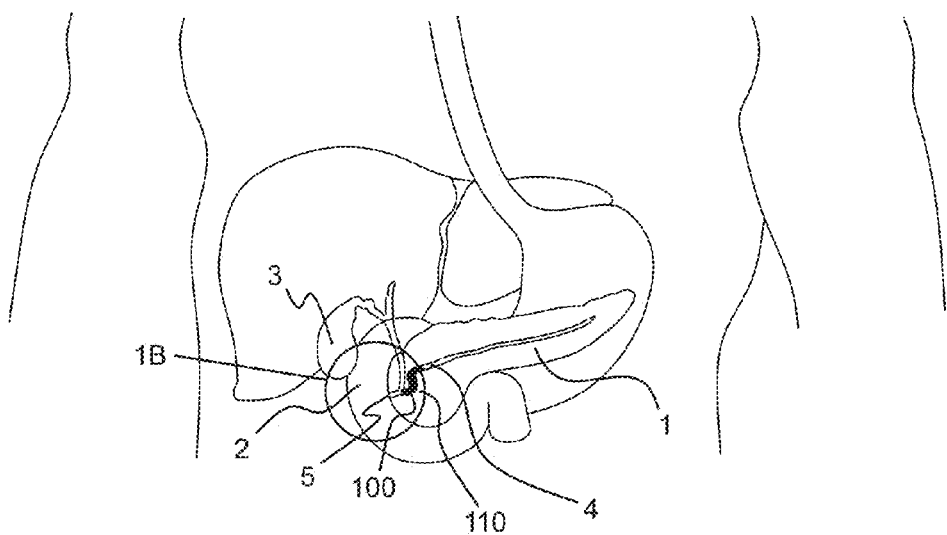
FIG. 1A is an anatomical view of the inventive medical device operationally positioned in a body of a patient.

While this invention can be embodied in many different forms, specific embodiments of the invention are described in detail herein. This description is an exemplification of the principles of the invention and is not intended to limit the invention to the particular embodiments illustrated.

The invention can be used in humans and used in non-human animals. This invention is suitable for use in the pancreas and for use in other organs and tissues. Although, illustrated embodiments refer to a stent being placed in the pancreatic duct, the inventive medical device can be used for performing a medical procedure in any body passageway including but not limited to gastrointestinal tract, the biliary tract, the urinary tract, the respiratory tract, the arteries and veins. Those skilled in the pertinent art will recognize that the use of the inventive medical device as described herein is not limited to the pancreas, but can be used in vascular conduits and other ductal systems such as a bile duct, a urinary tract, and the like in the human body. One aspect of the inventive medical device is to expand or open a passageway to allow flow of materials or air inside the body of a patient Various aspects of the invention are depicted in the figures. For the purposes of this disclosure, like reference numerals in the figures shall refer to like features unless otherwise indicated.

As used in the specification, the terms proximal and distal should be understood as being in terms of a physician delivering the medical device to a patient. The term "proximal" refers to an area or portion of the medical device or patient that is closest to the physician during a placement procedure. The term "distal" refers to an area or portion that is farthest from the physician.

FIG. 1A is an anatomical elevational view of a pancreas 1, duodenum 2, gall bladder 3, and adjacent portions of the alimentary canal. In one embodiment, the inventive medical device 100 is used to treat a narrowing or constriction of the pancreatic duct 4. The site of treatment is herein referred to as the target site 110.

Figure 1B:
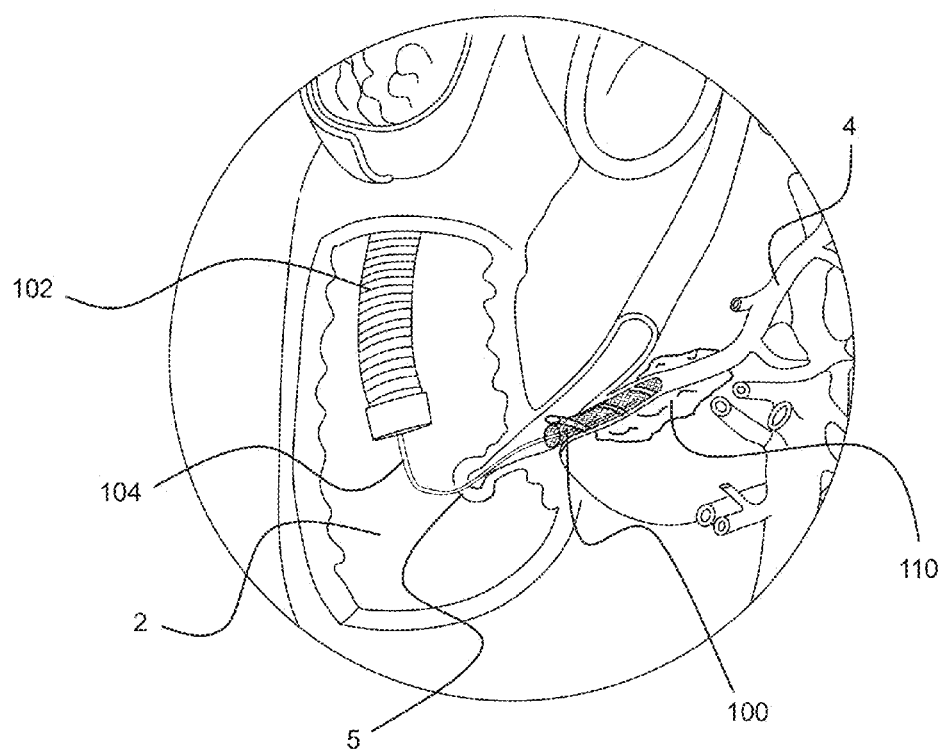
FIG. 1B is an enlarged view of the medical device in FIG. 1A positioned in the body of the patient.

FIG. 1B shows an enlarged view of the region where pancreatic duct 4 abuts duodenum 2. In at least one embodiment, medical device 100 is delivered to target site 110 by an endoscopic delivery catheter 102 that has been advanced from the esophagus (not shown) into duodenum 2. In some embodiments, medical device 100 is implanted using a delivery catheter 102 having a guide wire 104 that aids in placement of medical device 100. Guide wire 104 is advanced past the sphincter of Oddi 5 and along the pancreatic duct 4 to reach target site 110. Medical device 100 is shuttled from delivery catheter 102 along guide wire 104 to target site 110. In at least one embodiment, an introducer catheter (not shown) maintains medical device 100 in an unexpanded conformation and delivers unexpanded medical device 100 to target site 110. Once medical device 100 is properly positioned adjacent target site 110, medical device 100 is radially expanded so as to support and reinforce the vessel at target site 110. In some embodiments, medical device 100 is self-expanding and will radially expand once deployed. In some embodiments, the introducer catheter comprises an outer sheath that keeps medical device 100 in an unexpanded conformation. Once the introducer catheter reaches target site 110, the outer sheath of the introducer catheter is retracted, allowing medical device 100 to expand and engage the lumen wall of target site 110. In some embodiments, radial expansion of medical device 100 is accomplished by inflation of a balloon (not shown) attached to the introducer catheter.

Figure 2:
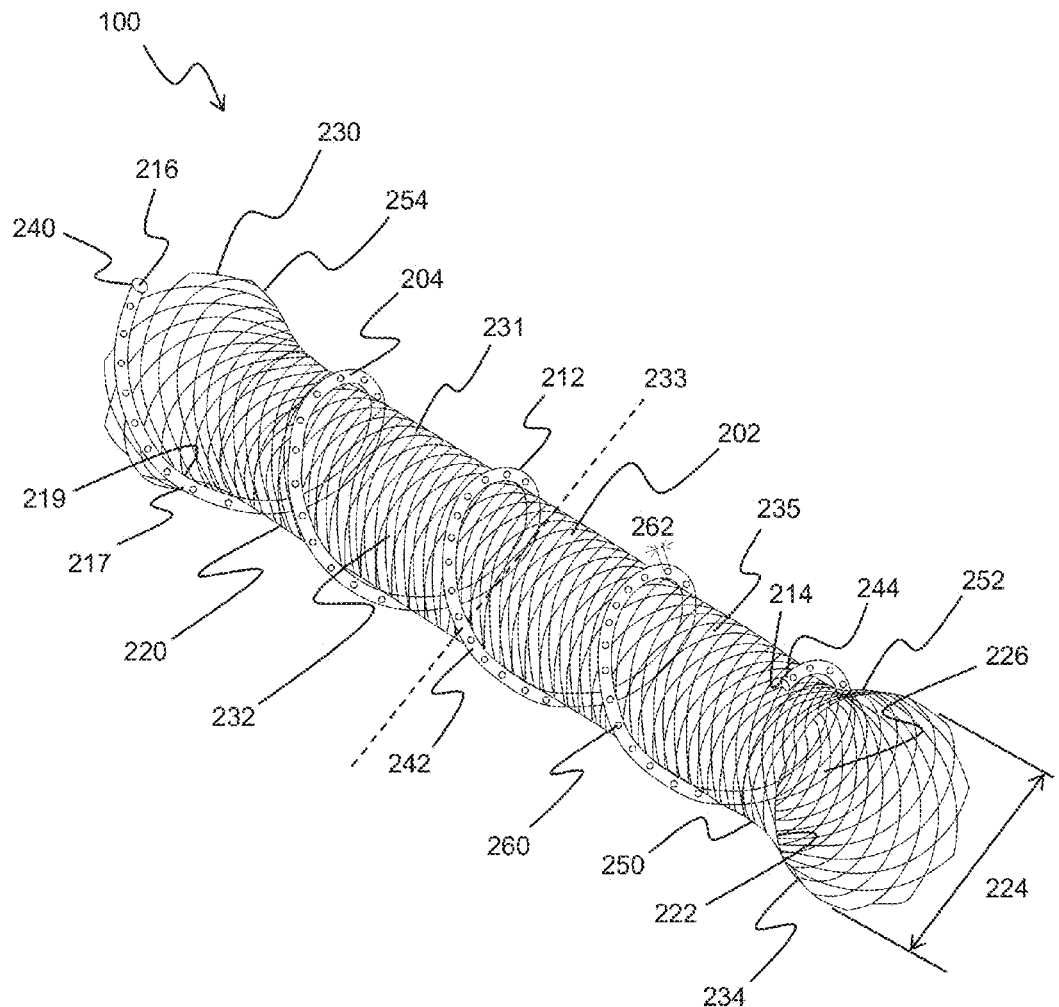
FIG. 2 is a perspective view of an embodiment of the inventive medical device comprising a stent and a drainage tube.

FIG. 2 is a perspective view of one embodiment of inventive medical device 100, wherein a drainage tube 204 wraps around at least a portion of the outer surface 220 of a stent 202. In some embodiments, drainage tube 204 is of similar design to a 3 French plastic stent made of a polyethylene material.

An outer surface 220 of stent 202 defines an outer diameter 224 of stent 202. An inner surface 222 of stent 202 defines a lumen 226 of stent 202. Stent 202 has a proximal end 230, a distal end 234, and a central region 232 located between proximal end 230 and distal end 234. Central region 232 has a mid-plane 233, which is equidistant from proximal end 230 and distal end 234. Stent 202 has a proximal region 231 and a distal region 235, wherein proximal region 231 is the region of stent 202 located between mid-plane 233 and proximal end 230, and distal region 235 is the region of stent 202 located between mid-plane 233 and distal end 234. In some embodiments, stent 202 is flared at at least one end so that outer diameter 224 in central region 232 is smaller compared to outer diameter 224 at proximal end 230 and/or distal end 234. Proximal flare 254 and distal flare 252 increase the anti-migratory ability of stent 202, thereby facilitating stent fixation. Proximal flare 254 resists migration of stent 202 in the proximal direction. Similarly, distal flare 252 resists migration of stent 202 in the distal direction. In some embodiments, proximal flare 254 and the distal flare 252 are constructed to readily conform to changes in body lumen walls during transmittal of bodily fluids or food. In some embodiments, stent 202 is self expanding and able to conform to changes in the body lumen walls thereby mitigating the need to replace stent 202 with another stent having a larger outer diameter 224.

In some embodiments, distal end 244 of drainage tube 204 is located at base 250 of distal flare 252, wherein base 250 of distal flare 252 is the portion of the distal flare 252 that is contiguous with central region 232 of stent 202. In some embodiments, stent 202 facilitates treatment of blockages present in the pancreatic duct. In at least one embodiment, stent 202 can be placed so that the proximal end 230 of stent 202 is proximate the ampulla of Vater so that the pancreatic fluid from the pancreatic duct can unite with the bile juices to form a mixture, which proceeds toward the sphincter of Oddi 5 and into the duodenum 2 to facilitate digestion of food. In at least one embodiment, proximal end 240 of drainage tube 204 is positioned adjacent to proximal end 230 of stent 202, allowing proximal end 240 of drainage tube 204 to empty into the duodenum when proximal end 230 of stent 202 is positioned proximal to the sphincter of Oddi 5. In some embodiments, stent 202 includes radiopaque markers made of gold or any other radiopaque material suitable for implantation. The radiopaque markers aid fluoroscopic imaging of stent 202 during placement of stent 202. In some embodiments, the radiopaque markers are incorporated at the proximal flare 254 and/or the distal flare 252 of stent 202.

In some embodiments, stent 202 is flexible and elastomeric in nature, allowing stent 202 to be radially compressed for intraluminary catheter implantation. Stent 202 can be any type of expandable stent, such as laser cut or braided designs. In some embodiments, outer surface 220 of stent 202 has a substantially uneven structure. The uneven structure increases the amount of frictional force between the body lumen walls and the outer surface 220 of the stent 202 thereby increasing anti-migratory properties of stent 202. In at least one embodiment, stent 202 is cylindrical. In some embodiments, stent 202 has an annular transverse cross-section. The transverse cross-section of stent 202 may be circular or non-circular, having a uniform bore or non-uniform bore.

Stent 202 or portions thereof can be metal, including but not limited to shape memory metal such as nitinol. Stent 202 and drainage tube 204 or portions thereof can be fabricated using shape memory polymers, or simple elastic medical-grade polymers, or medical-grade plastically expandable materials. Examples of some suitable materials include but are not limited to expanded polytetrafluoroethylene (ePTFE), polytetrafluoroethylene which is not expanded, polyurethane olefin polymers, polyethylene, polypropylene, polyvinyl, polyvinyl chloride, fluorinated ethylene propylene copolymer, polyvinyl acetate, polystyrene, polyethylene terephthalate (PET) polyesters, naphthalene dicarboxylate derivatives, such as polyethylene naphthalate, polybutylene naphthalate, poly trimethylene naphthalate and trimethylenediol naphthalate, polyurethane, polyurea, silicone rubbers, polyamides, polycarbonates, polyaldehydes, natural rubbers, polyester copolymers, styrene-butadiene copolymers, polyethers, such as fully or partially halogenated polyethers, copolymers, polyesters, including, polyolefins, polymethyl acetates, polyamides, naphthalane dicarboxylene derivatives, natural silk, and combinations thereof. Stent 202 and drainage tube 204 can be made from biodegradable or bioabsorbable materials. Stent 202 can be formed of biocompatible materials, such as polymers which may include fillers such as metals, carbon fibers, glass fibers or ceramics.

Drainage tube 204 has an external surface 212 and an internal surface 214, which defines a lumen 216 of drainage tube 204. Drainage tube 204 has an intermediate portion 242, which connects proximal end 240 to distal end 244. Drainage tube 204 includes a plurality of drainage holes 260, which connect external surface 212 to internal surface 214. In some embodiments, drainage holes 260 are fabricated along at least a portion of intermediate portion 242. Drainage holes 260 facilitate flow of pancreatic fluid to the duodenum 2 by providing a pathway for the pancreatic fluid to access lumen 216 of drainage tube 204.

In at least one embodiment, drainage tube 204 wraps around stent 202 so that proximal end 240 of drainage tube 204 is positioned adjacent to the proximal end 230 of stent 202. In some embodiments, drainage tube 204 wraps around only a portion of stent 202. For example, in at least one embodiment drainage tube 204 wraps around stent 202 from the proximal end 230 of stent 202 to mid-plane 233 of stent 202 so that distal end 244 of the drainage tube 204 is adjacent to mid-plane 233 of stent 202. In some embodiments, distal end 244 of drainage tube 204 lies distal of mid-plane 233 of stent 202. In some embodiments, distal end 244 of drainage tube 204 lies proximal of mid-plane 233 of stent 202. In some embodiments, drainage tube 204 wraps around the entire length of stent 202 so that proximal end 240 of drainage tube 204 is adjacent to proximal end 230 of stent 202, and distal end 244 of drainage tube 204 is adjacent to distal end 234 of stent 202.

In some embodiments, drainage tube 204 wraps helically around outer surface 220 of stent 202. External surface 212 of drainage tube 204 includes two portions—a first portion 217 that is in contact with a body lumen wall, and a second portion 219 that is in contact with outer surface 220 of stent 202. In at least one embodiment, second portion 219 of drainage tube 204 is secured to outer surface 220 of stent 202 at one or more discrete points of contact between drainage tube 204 and outer surface 220, allowing drainage tube 204 to slide along and maintain contact with outer surface 220 as stent 202 radially expands. In at least one embodiment, drainage tube 204 is secured to outer surface 220 by at least one of an adhesive coupling, thermal coupling, and mechanical coupling.

In some embodiments, first portion 217 includes a plurality of drainage holes 260 while second portion 219 does not contain any drainage holes 260. Placement of drainage holes 260 on external surface 212 is defined by an angular coordinate that is referenced to a polar coordinate system located centrally within lumen 216 of drainage tube 204. Such a coordinate system is shown in FIGS. 5B and 6B. In the reference coordinate system, an angle of 0° refers to the mid-line of second portion 219. Placement of drainage holes 260 is also defined by a longitudinal coordinate that specifies the distance of travel along drainage tube 204 from proximal end 240. In at least one embodiment, all drainage holes 260 have the same angular coordinate. In some embodiments, at least two drainage holes 260 have different angular coordinates. In some embodiments, two or more drainage holes 260 have the same longitudinal coordinate and a different angular coordinate. In some embodiments, drainage holes 260 are uniformly spaced along the longitudinal coordinate direction. In some embodiments, drainage holes 260 are non-uniformly spaced along the longitudinal coordinate direction.

External surface 212 of drainage tube 204 defines a transverse cross-sectional shape. The transverse cross-sectional shape of drainage tube 204 can be any geometry that can be extruded or molded and allow fluid to pass without creating permanent anchoring points of pancreatic tissue. In some embodiments, external surface 212 defines a circular transverse cross-sectional shape. In at least one embodiment, external surface 212 defines a transverse cross-sectional shape that is an oval. In some embodiments, drainage tube 204 has a variable internal and/or external diameter. In at least one embodiment, drainage tube 204 has a uniform lumen 216 and a uniform transverse cross-sectional shape. In some embodiments, lumen 216 is non-uniform. In at least one embodiment, the diameter of lumen 216 is smaller in the distal region of drainage tube 204 compared with the diameter of lumen 216 in the proximal region of drainage tube 204.

Drainage holes 260 have a width 262. In at least one embodiment, all drainage holes 260 have the same width 262. In some embodiments, at least two drainage holes 260 have different widths 262 from one another. In some embodiments, width 262 of each drainage hole 260 varies from 0.005 inches to 0.015 inches. In at least one embodiment, width 262 is 0.010 inches. In some embodiments, drainage holes 260 are oval shaped or circular. In some embodiments, drainage holes 260 are different shapes other than the circular shape or oval shape. For example, in some embodiments drainage holes 260 have an elliptical shape or a polygonal shape, such as a square or a rectangular cross-sectional shape. In some embodiments, all drainage holes 260 have the same shape. In some embodiments, at least two drainage holes 260 have different shapes from one another. In at least one embodiment, the shape of drainage hole 260 tapers as drainage tube 204 is traversed. For example, in at least one embodiment all drainage holes 260 are circular with the width 262 of the drainage holes 260 decreasing as the drainage tube 204 is traversed in the distal direction.

Figure 3:
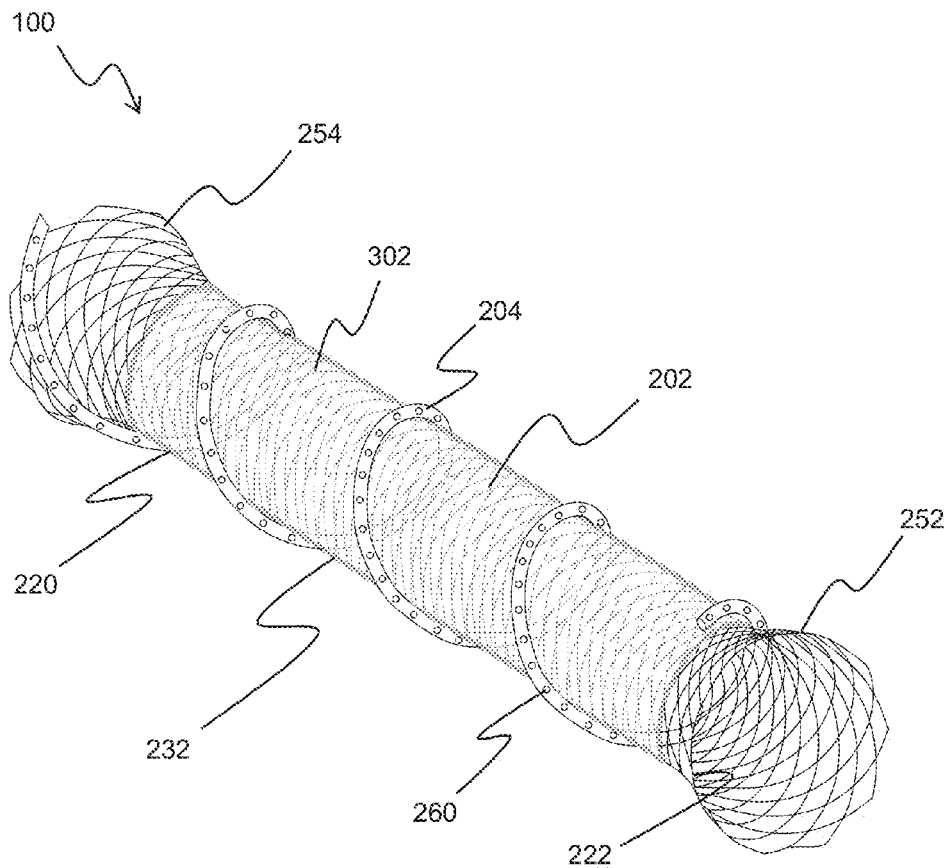
FIG. 3 is a perspective view of an embodiment of the inventive medical device comprising a stent, a drainage tube, and a covering disposed on the outer surface of the stent.

FIG. 3 is a perspective view of the inventive medical device 100, in accordance with an embodiment of the invention. In some embodiments, medical device 100 includes a covering 302 attached to stent 202. In some embodiments, covering 302 is disposed on outer surface 220 of stent 202. In some embodiments, covering 302 is an integral part of outer surface 220 of stent 202. In some embodiments, covering 302 extends over the entire central region 232 of the stent 202. In some embodiments, covering 302 extends over some but not all of central region 232. In at least one embodiment, outer surface 220 of stent 202 is free from covering 302 at proximal flare 254 and distal flare 252 to preserve the anti-migratory ability of stent 202. In some embodiments, covering 302 is disposed on outer surface 220 of stent 202 at proximal flare 254 and distal flare 252.

Figure 4A:
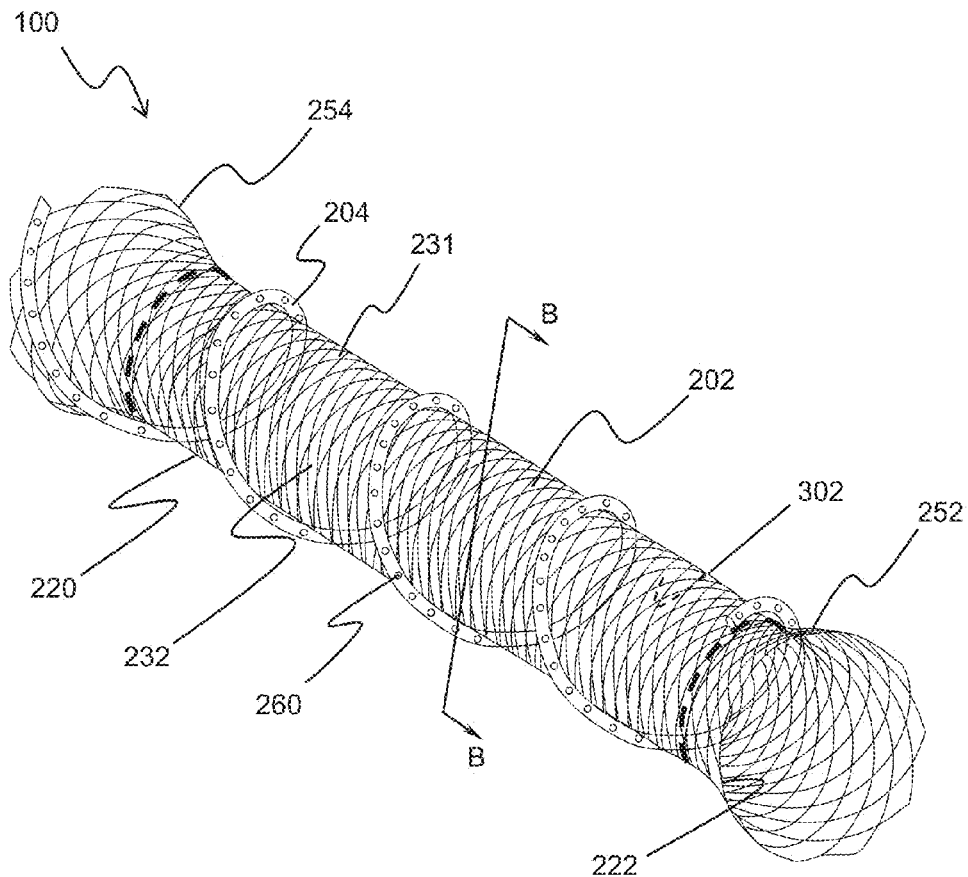
FIG. 4A is a perspective view of an embodiment of the inventive medical device comprising a stent, a drainage tube, and a covering disposed on an inner surface of the stent.
Figure 4B:
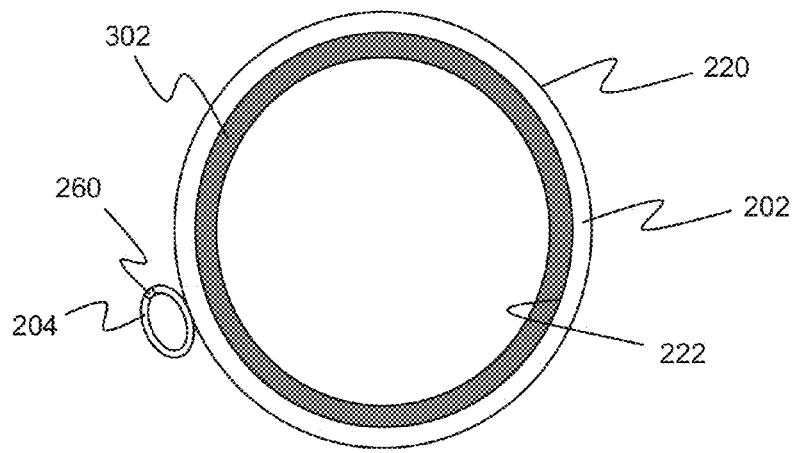
FIG. 4B is an end view of the drainage tube of FIG. 4A.

In some embodiments, covering 302 is disposed on inner surface 222 of stent 202. FIG. 4A is a perspective view of one embodiment of medical device 100 having a covering 302 disposed on inner surface 222 of stent 202. FIG. 4B is an end view of the embodiment of medical device 100 depicted in FIG. 4A. In some embodiments, covering 302 is attached to inner surface 222 of stent 202. In at least one embodiment, covering 302 is an integral part of inner surface 222 of stent 202. In some embodiments, covering 302 extends over the entire central region 232 of stent 202. In some embodiments, covering 302 extends over some but not all of central region 232. In at least one embodiment, covering 302 is disposed on inner surface 220 of stent 202 at proximal flare 254 and distal flare 252. In some embodiments, inner surface 220 of stent 202 is free from covering 302 at proximal flare 254 and distal flare 252.

In some embodiments, covering 302 is made of a material selected from the group consisting of silicone, urethane, biocompatible materials, and combinations thereof. In some embodiments, covering 302 is made of polytetrafluoroethylene (PTFE).

In some embodiments, covering 302 makes stent 202 less susceptible to invasion from surrounding tissue. In at least one embodiment, covering 302 increases patency by reducing the area of stent 202 that is available as a scaffold for accumulation of undesired substances that lead to occlusion. Few exemplary situations leading to occlusion include but are not limited to sludge formation, tumor overgrowth, tumor ingrowth, food debris, or stone formation.

Figure 5A:
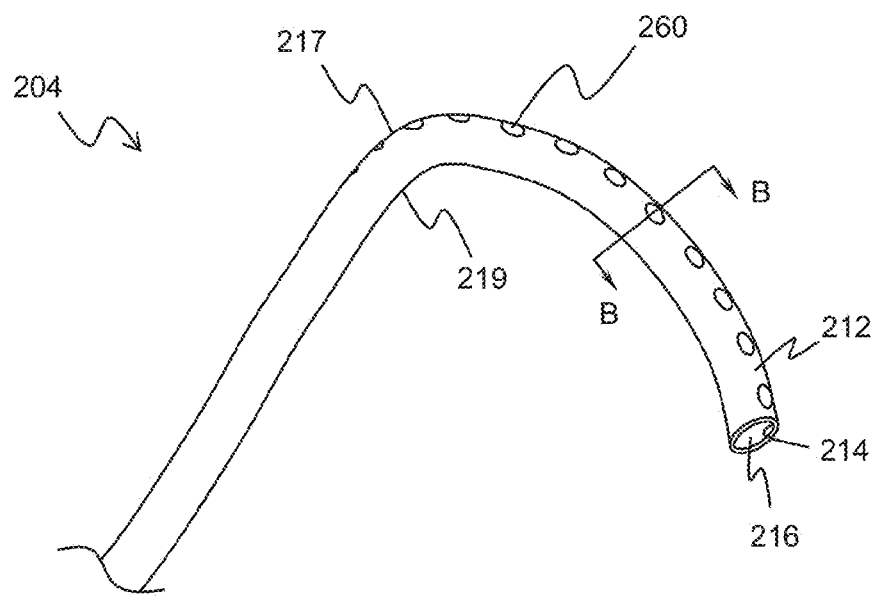
FIG. 5A is a perspective view of a portion of an embodiment of a drainage tube with a circular cross-section.
Figure 5B:
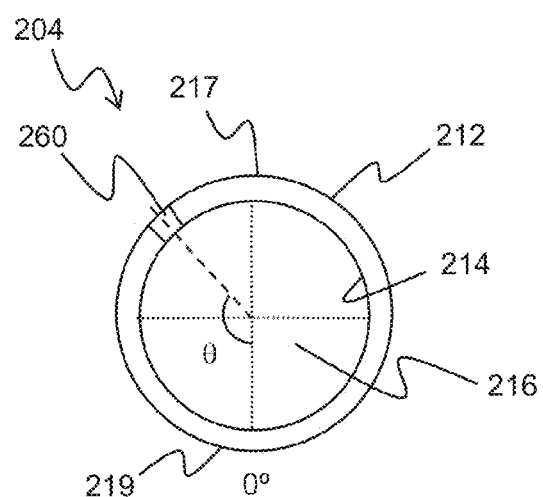
FIG. 5B is an end view of the drainage tube of FIG. 5A.

FIG. 5A is a perspective view of one embodiment of drainage tube 204 that has a circular cross-section. FIG. 5B is an end view of the drainage tube 204 of FIG. 5A.

Figure 6A:
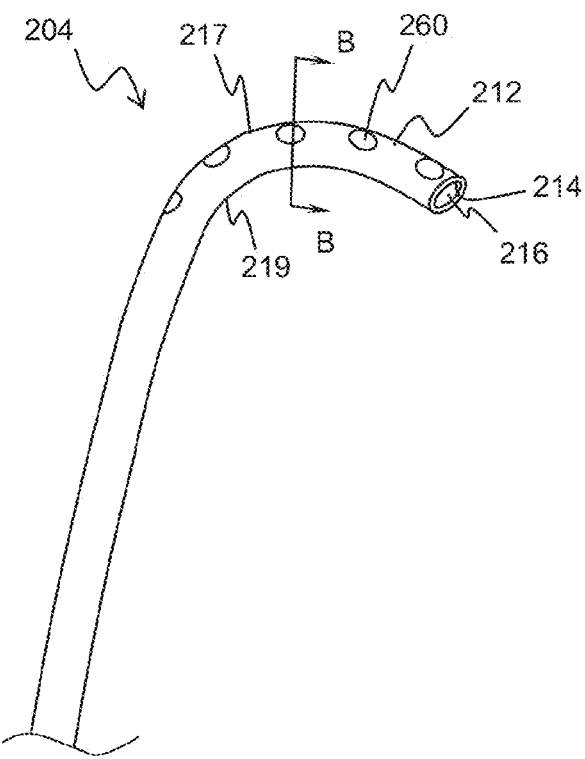
FIG. 6A is a perspective view of a portion of an embodiment of a drainage tube with an oval cross-section.
Figure 6B:
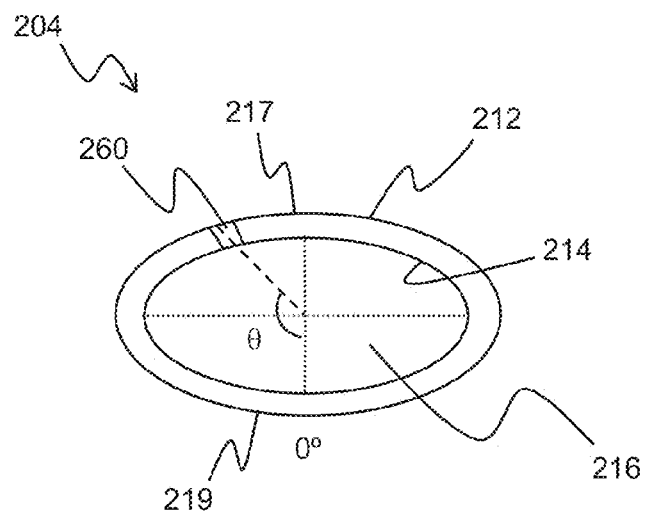
FIG. 6B is an end view of the drainage tube of FIG. 6A.

FIG. 6A is a perspective view of one embodiment of drainage tube 204 that has an oval cross-section. FIG. 6B is an end view of the drainage tube 204 of FIG. 6A. The oval geometry can be configured to minimize the overall profile of the stent 202 and still provide a passage for the pancreatic fluid. The oval geometry of the transverse cross-section can be helpful in mechanical traction to prevent migration. In some embodiments, the transverse cross section of external surface 212 of drainage tube 204 can be of a different shape other than the circular-shape or the oval-shape. For example, the cross-sectional shape of drainage tube 204 can be an elliptical shape or polygon shape, such as a square or a rectangular cross-sectional shape.

A description of some exemplary embodiments of the invention can be contained in the following numbered paragraphs:

1. A medical device equipped with a drainage feature, the device comprising:
   a stent having a proximal end, a distal end, and an outer surface; and
   a drainage tube having a proximal end, a distal end, an internal surface, and an external surface, the external surface having a plurality of drainage holes, the drainage holes connecting to the internal surface, the drainage tube being attached to the outer surface of the stent.

2. The medical device of claim 1 wherein the proximal end of the drainage tube is positioned adjacent to the proximal end of the stent.

3. The device of claim 1 wherein the drainage tube wraps around the outer surface of the stent.

4. The device of claim 3 wherein the drainage tube helically wraps around the outer surface of the stent.

5. The device of claim 1 wherein the external surface of the drainage tube has a transverse cross section which is oval-shaped.

6. The device of claim 1 wherein the external surface of the drainage tube has a transverse cross section which is circular.

7. The device of claim 1 wherein internal surface of the drainage tube has a length and a transverse cross section, the transverse cross section varying in size along the length of the drainage tube.

8. The device of claim 1 wherein at least one of the distal and proximal ends of the stent is flared.

9. The device of claim 1 wherein at least a portion of the stent is made of a material selected from a group consisting of metals, polymeric materials, biodegradable materials, bioabsorbable materials, and combinations thereof.

10. The device of claim 1 wherein at least a portion of the drainage tube is made of a material selected from a group consisting of polymeric materials, biodegradable materials, bioabsorbable materials, and combinations thereof.

11. The device of claim 1 wherein each of the plurality of holes has a diameter of about 0.010 inch.

12. The device of claim 1 wherein at least one of the plurality of holes is oval-shaped.

13. The device of claim 1 wherein the plurality of holes vary in size and shape.

14. The device of claim 1 wherein the stent further comprises a covering, the covering surrounding the outer surface of the stent and being made of a material selected from a group consisting of silicone, urethane, biocompatible materials, and combinations thereof.

15. The medical device of claim 1, wherein the stent is of a braided type.

16. The medical device of claim 1, wherein the drainage tube is secured over the external surface of the stent by at least one of an adhesive coupling, thermal coupling, and mechanical coupling.

17. The medical device of claim 1, wherein the drainage tube includes a first portion exposed to a body lumen wall and a second portion in contact with the stent, wherein the plurality of holes are provided along at least a portion of the drainage tube such that the plurality of holes stay at the first portion and are exposed to the body lumen wall.

This completes the description of the invention. Those skilled in the art can recognize other equivalents to the specific embodiment described herein which equivalents are intended to be encompassed by the claims attached hereto.

What is claimed is:

1. A medical device equipped with a drainage feature, the device comprising:
   a stent having a proximal end, a distal end, and an outer surface, wherein the stent defines a lumen extending therethrough; and
   a drainage tube having a proximal end, a distal end, an internal surface, and an external surface, the external surface having a first portion configured to contact a body lumen wall and a second portion attached to the outer surface of the stent, the first portion of the external surface having a plurality of drainage holes connecting to the internal surface, such that the plurality of holes are configured to contact the body lumen wall, wherein the drainage tube wraps around the outer surface of the stent, and wherein any openings of the drainage tube open external to the lumen of the stent.

2. The medical device of claim 1 wherein the proximal end of the drainage tube is positioned adjacent to the proximal end of the stent.

3. The medical device of claim 1 wherein the drainage tube helically wraps around the outer surface of the stent.

4. The medical device of claim 1 wherein the external surface of the drainage tube has a transverse cross section of an oval-shape.

5. The medical device of claim 1 wherein the external surface of the drainage tube has a transverse cross section of a circular-shape.

6. The medical device of claim 1 wherein the drainage tube has a length and a transverse cross section, the external surface of the drainage tube defining the transverse cross section, the transverse cross section varying in size along the length of the drainage tube.

7. The medical device of claim 1 wherein at least one of the distal and proximal ends of the stent is flared.

8. The medical device of claim 1 wherein at least a portion of the stent is made of a material selected from a group consisting of metals, polymeric materials, biodegradable materials, bio-absorbable materials, and combinations thereof.

9. The medical device of claim 1 wherein at least a portion of the drainage tube is made of a material selected from a group consisting of polymeric materials, biodegradable materials, bio-absorbable materials, and combinations thereof.

10. The medical device of claim 1 wherein each of the plurality of holes has a diameter of 0.005 to 0.015 inch.

11. The medical device of claim 1 wherein at least one of the plurality of holes is oval-shaped.

12. The medical device of claim 1 wherein the plurality of holes vary in size and shape.

13. The medical device of claim 1 wherein the stent further comprises a covering, the covering surrounding the outer surface of the stent and being made of a material selected from a group consisting of silicone, urethane, biocompatible materials, and combinations thereof.

14. The medical device of claim 1, wherein the stent is of a braided type.

15. The medical device of claim 1, wherein the drainage tube is secured over the external surface of the stent by at least one of an adhesive coupling, thermal coupling, and mechanical coupling.

16. The medical device of claim 1, wherein the plurality of holes are provided along at least a portion of the drainage tube.

* * * * *